United States Patent
Kuisell et al.

[11] Patent Number: 5,817,920
[45] Date of Patent: Oct. 6, 1998

[54] OXYGEN SENSOR WITH ANNULAR SUPPORT MEMBER PROVIDING IMPROVED MECHANICAL SHOCK RESISTANCE

[75] Inventors: Richard Courtney Kuisell, Papeer; David Earl Achey, Grand Blanc; Richard William Duce, Flushing, all of Mich.

[73] Assignee: General Motors Corporation, Detroit, Mich.

[21] Appl. No.: 819,785

[22] Filed: Mar. 18, 1997

[51] Int. Cl.⁶ .......................... G01N 27/26; G01N 27/12
[52] U.S. Cl. .......................... 73/23.31; 338/229; 204/424
[58] Field of Search ................. 73/23.31, 23.32; 338/34, 229; 204/424, 426

[56] References Cited

U.S. PATENT DOCUMENTS

| | | | |
|---|---|---|---|
| 4,225,842 | 9/1980 | Schlesselman et al. | 73/23.31 X |
| 4,234,542 | 11/1980 | Romine | 73/23.31 X |
| 4,282,080 | 8/1981 | Muller | 204/195 |
| 4,403,207 | 9/1983 | Murphy et al. | 338/34 |
| 4,462,891 | 7/1984 | Lawless | 204/427 |
| 4,535,316 | 8/1985 | Wertheimer et al. | 73/23.32 X |
| 4,559,126 | 12/1985 | Mase et al. | 204/425 |
| 4,574,042 | 3/1986 | Shiraishi | 204/429 |
| 4,980,044 | 12/1990 | Ker | 204/426 |
| 5,098,548 | 3/1992 | Duce | 204/424 |
| 5,246,562 | 9/1993 | Weyl et al. | 204/424 |
| 5,329,806 | 7/1994 | McClanahan et al. | 73/31.05 |
| 5,467,636 | 11/1995 | Thompson | 73/23.31 |
| 5,627,306 | 5/1997 | Yamauchi et al. | 204/424 X |

*Primary Examiner*—Michael Brock
*Attorney, Agent, or Firm*—Anthony Luke Simon

[57] ABSTRACT

An oxygen sensor comprising: an elongated planar sensing element; a tubular shield within which at least a portion of the sensing element extends; a seal sealably mounting the sensing element within the tubular shield; a shell for mounting the oxygen sensor to a body through which exhaust flows; and an annular gasket seating at a first surface the tubular shield and at a second surface an annular seat of the shell, wherein there is no direct contact between the tubular shield and the shell. An advantage of improved shock resistance is obtained, preventing damage to the seal, which may be made of glass.

20 Claims, 3 Drawing Sheets

OXYGEN SENSOR WITH ANNULAR SUPPORT MEMBER PROVIDING IMPROVED MECHANICAL SHOCK RESISTANCE

This invention relates to an oxygen sensor. The subject of this invention is related to the subject of pending patent application Ser. No. 08/600,136, assigned to the assignee of this invention.

BACKGROUND OF THE INVENTION

Exhaust oxygen sensors have been used for many years in automotive vehicles to sense the presence of oxygen in exhaust gasses, for example, to sense when an exhaust gas content switches from rich to lean or lean to rich. One known type of oxygen sensor includes a flat plate oxygen sensor formed of various layers of ceramic and electrolyte materials laminated and sintered together with electrical circuit and sensor traces placed between the layers in a known manner.

Because automotive oxygen sensors are mounted to members of the vehicle exhaust flow system, the sensors must be durable, able to withstand vibration and jarring such as would occur during installation and normal vehicle operation and able to withstand shock from the occasional stone or other small road debris that may happen to be thrown at the sensor, for example, by the vehicle's tires.

SUMMARY OF THE INVENTION

It is an object of this invention to provide an oxygen sensor according to claim 1.

Advantageously this invention provides an oxygen sensor for use in an automotive vehicle exhaust system with improved durability.

Advantageously, this invention provides an oxygen sensor suitable for use in a motor vehicle with improved resistance to mechanical shock and more robustness for a rugged vehicle environment.

Advantageously, this invention provides an oxygen sensor with a structure that mechanically decouples the internal sensing element and its associated fragile structures, such as an internal sensor glass seal, from the sensor shell. This mechanical decoupling minimizes the chance that mechanical shock to the sensor will travel through the shell and damage the sensor components such as the glass seal.

Advantageously, then, according to a preferred example, this invention provides an oxygen sensor comprising an elongated planar sensing element, a tubular shield within which at least a portion of the sensing element extends, a seal sealably mounting the sensing element within the tubular shield, a shell for mounting the housing to a body through which exhaust gas flows and an annular gasket having a first surface seating the tubular shield and a second surface seated in an annular seat of the shell, wherein there is no direct contact between the tubular shield and the shell. Preferably, the gasket provides a gas-resistant and supporting seal between the tubular shield and the shell.

BRIEF DESCRIPTION OF THE DRAWINGS

The present invention will now be described by way of example with reference to the following figures, in which.

DETAILED DESCRIPTION OF THE INVENTION

Figure 1:
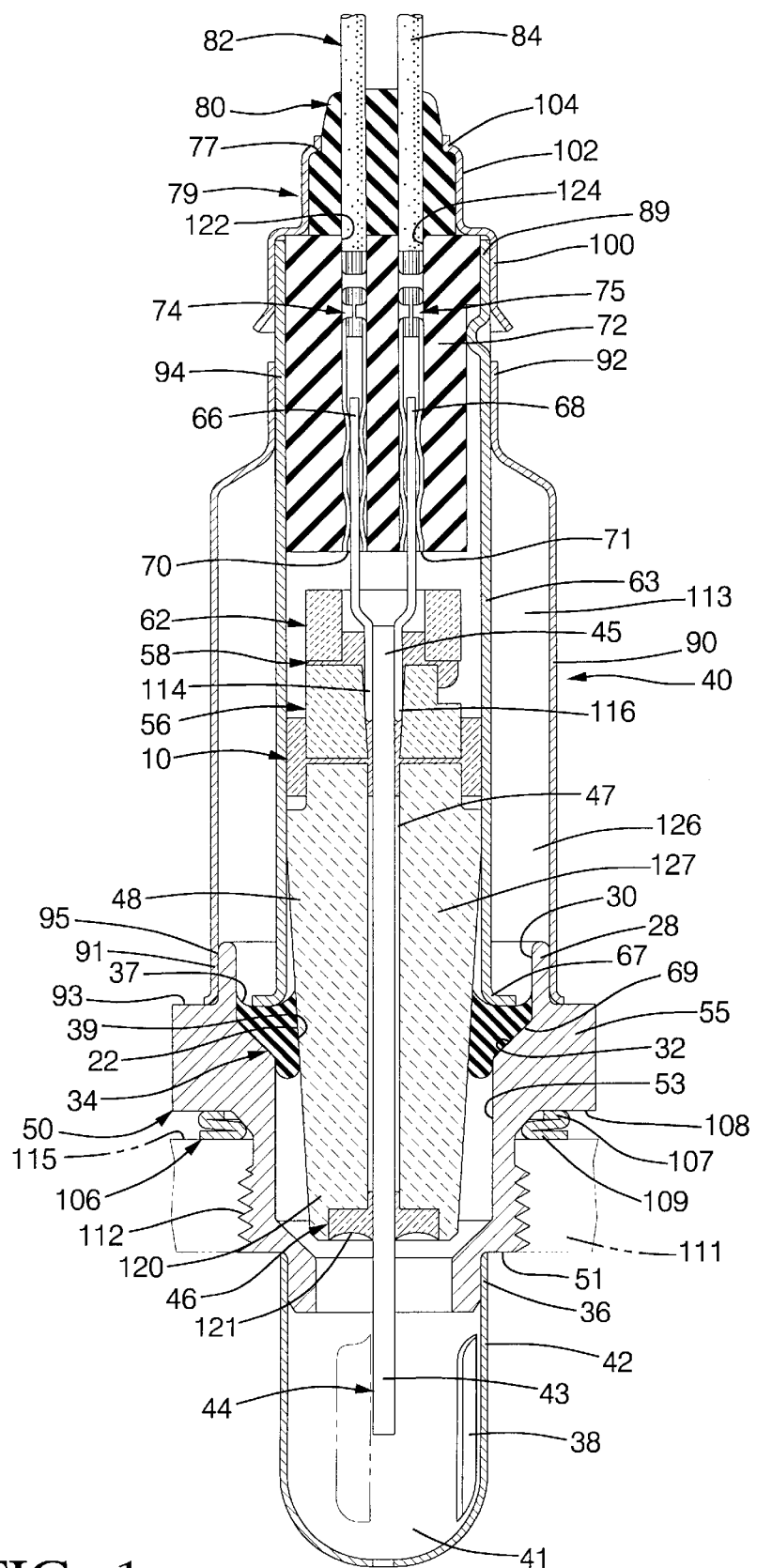
FIG. 1 illustrates an example oxygen sensor according to this invention.

Referring now to FIG. 1, the example oxygen sensor shown includes a housing structure generally formed of upper shield 63, lower shield 42, outer shield 90 and shell 50. Terminal adapter 72, upper insulator 62, wedge ring 56, lower insulator 48 and a portion of sensing element 44 are located within the upper shield 63. The sensing element 44 is an exhaust oxygen sensing element of a known type with a generally flat elongated rectangular shape. A first end 43 of sensing element 44 includes an oxygen-responsive structure fabricated into the sensing element 44 in a known manner, preferably along with a heater of a known type. At the opposite end 45 of the sensing element 44, the lower ends 114 and 116 of terminals 66 and 68 contact external pads (not shown) on the end 45 to provide electrical connection between the female terminals 74 and 75 and the sensing element 44. The ends 114 and 116 of the terminals 66 and 68 are maintained against the end 45 of the sensing element 44 by a wedge ring 56 having an internal wedged shaped opening pressed against the ends 114 and 116 forcing them in place against the terminal pads on end 45 of sensing element 44.

An upper insulator 62 is maintained in place above the wedge ring by glass support 58. Below the wedge ring 56, a long insulator 48, that acts as a thermal and electrical insulator as well as a support member, extends from close to the wedge ring 56 to the sensing chamber 41 where end 43 of the sensing element 44 is located. A glass seal 10 supports the sensing element 44 within upper shield 63 and provides sealing engagement between the sensing element 44 and upper shield 63, forming a gas-tight barrier between the sensing element ends 43 and 45.

The glass seal 10 has a flat circular disk portion, including a centrally located rectangular opening in which the planar sensing element 44 is located. At an outer radial periphery of the flat disk portion, the seal forms a circular cylindrical wall extending axially away from the flat circular disk portion in first and second directions opposite to each other. The outer periphery of the circular cylindrical wall engages and bonds with the inner cylindrical wall of the upper shield 63 and the inner periphery of the circular cylindrical wall engages and bonds with the wedge ring 56 and the lower insulator 48, as do the top and bottom planar surfaces of the flat disk portion. The rectangular opening engages and bonds to the planar sensing element 44. When the assembly shown is heated to melt and bond the glass seal, glass flow and capillary action draw the glass between the sensing element 44 and the inner openings of the wedge ring 56 and the lower insulator 48. An example suitable glass seal 10 is described in the above-mentioned pending application Ser. No. 08/600,136, having a disclosure incorporated herein by reference.

The lower insulator 48 has a central opening 47 through which the sensing element 44 passes. The sensing element 44 is secured near the sensing end 43 by a glass support 46 bonded to the sensing element 43 and to the lower end 120 of the lower insulator 48 within recess 121.

Figure 3:
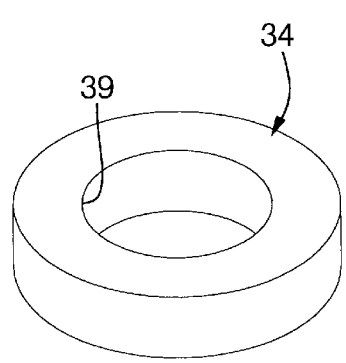
FIG. 3 illustrates an example gasket for use with the oxygen sensors shown in FIGS. 1 and 2.

In the example shown, the lower end 67 of the upper shield 63 extends to a middle portion 127 of the lower insulator 48 so that the lower end 120 of lower insulator 48 extends out from the upper shield 63. The shell 50 has an inner cylindrical opening 53 wide enough to accommodate passage of the lower insulator 48 without direct contact between the shell 50 and the lower insulator 48. End 67 of the upper shield 63 is seated sealingly in the annular depression 37 formed in gasket 34 by compression that occurs during assembly. More particularly, before assembly, the gasket 34 has the shape shown in FIG. 3. Because the gasket, in the preferred example, is formed of an ceramic fibrous material bonded by an vermiculite material of a known type such as used for matting in catalytic converter assemblies, the gasket 34 deforms in response to the compression forces between the lower end 67 of upper shield 63 and the cylindrical and conical inner surfaces 30 and 32 of the shell 50 to take on the shape shown in FIG. 1. Additionally, the outer surface 22 of the lower insulator 48 forms a wedge shape, with the wide end of the wedge proximate to seal 10 and the narrow end 120 proximate to the sensing chamber 41. The wedge shape provides radially outward compressive forces between the lower insulator 48 and the shell 50 so that the gasket 34 is compressed radially outwardly from surface 39. As is shown in FIG. 1, the lower end 67 of the upper shield 63 is preferably flared out to provide a compressing surface against gasket 34. Through the compressive forces, the gasket 34 provides gas-resistant sealing and compliant (non-rigid) supporting engagement to the upper shield 63 and to the shell 50. The conical surface 32 orients the surface 69 of the gasket 34 into the preferred direction for thermal expansion of gasket 34.

The shell 50 includes a body portion 55 and threaded portion 112. The body portion 55 is shaped to accommodate a wrench or other tool for tightening the threaded portion 112 into a mount welded to an exhaust pipe or other component of an exhaust flow system, enabling the sensing chamber 41 to be located within a flow of exhaust gasses to be measured. An annular gasket 106 has a first axial end 107 that rests against shoulder 108 of the body portion 55 of the shell 50 and a second axial end 109 that rests against the surface 115 of the mount 111 when the shell 50 is threadably engaged thereto.

The lower shield 42 defines the chamber 41 and includes a plurality of vents 38 for allowing passage of exhaust gas into and out of the chamber 41 so that the gasses may be sensed by the sensing element 44. An open end 36 of the lower shield 42 is mounted against the shoulder 51 of the shell 50 and may be welded in place or held in place by a secure friction fit.

At the upper end of the upper shield 63, the terminals 66 and 68 engage female terminal slots 70 and 71 of the terminals 74 and 75, which are connected to the electrical wires 82 and 84 in a known manner. The terminals 74 and 75 are tightly fit in the cylindrical openings 122, 124 passing through the terminal adapter 72. The wires 82 and 84 pass through the cable seal 80, generally comprising a rubber material suitable for use in a high temperature environment, and extend into the passages 122, 124 of the terminal adapter 72. The seal 80 is maintained in place by the metal retainer 79 having an end 104 forming a seat around the shoulder 77 of the seal 80, a central portion 102 around the lower portion of the seal 80 and a lower end 100 forming a cylindrical opening tightly fit around the upper end 89 of the upper shield 63. The retainer 79 is preferably welded or otherwise secured in a leak-proof manner to the upper end 89 of the upper shield 63.

The outer shield 90 has an upper end 92 of reduced diameter to provide a tight fit around the outer surface of the portion 94 of the upper shield 63 and is held in place by either a weld, braze or a tight friction fit. The body of the outer shield 90 is expanded radially outward from the upper shield 63 providing an annular space 113 between the upper shield 63 and the outer shield 90. The lower end 91 of the protective shield 90 fits around the outer cylindrical surface 95 of the extending end 28 of the shell 50 and abuts against seat 93. Lower end 91 is held in place by either a tight friction fit or a weld. If desired, a packing material may be placed around the lower portion of the upper shield 63 in the annular region 126 between the upper shield 63 and the outer shield 90. The packing material, for example a packed wire mesh or other compliant material, may serve to provide added support if necessary or desirable. Because the outer shield 90 is affixed to both the upper shield 63 and the shell 50, the outer shield 90 mechanically holds the upper shield 63, the gasket 34 and the shell 50 in compressive force engagement.

For the structure shown in FIG. 1, example material for the shields 42, 63 and 90 and for the shell 50 is high chrome or high nickel stainless steel, all steels chosen for high temperature endurance, high-strength and corrosion resistance. The terminal adapter 72 may be a plastic or ceramic durable in the high temperature environments to which oxygen sensors are exposed and the upper insulator 62, wedge ring 56 and lower insulator 48 may comprise steatite, alumina, ceramic or other suitable high temperature material providing the desired support, strength and thermal and electrical insulating properties described herein. The glass seal 10 preferably is formed of glass having a melting temperature higher than the expected operating temperature of the sensor at the region of the glass seal 10 and having a coefficient of thermal expansion appropriate to maintain the gas tight seal with the upper shield 63.

In assembly of the upper and lower insulators 62 and 48, the wedge ring 56, the glass supports 58 and 46 and the glass seal 10 are located within the upper shield 63 in their respective relative positions as shown in FIG. 1 and are placed in an oven where they are brought to a temperature higher than the melting temperature of the glass, allowing the glass to flow into sealing and bonding contact with the respective members shown. The oven is then controllably cooled so that the glass becomes more solid to provide the structural and sealing properties described herein. The rest of the sensor is then assembled to take the structure shown.

The annular gasket 34 preferably comprises a high temperature durable fibrous material, such as a ceramic fiber material, bonded together by a vermiculite or other suitable bonding material. In the preferred example, the vermiculite bonding material is of a known type, for example, used as support matting in catalytic converter assemblies, that expands when heated to maintain a sealing function between the shell 50 and gasket 34 and between the gasket 34 and lower end 67 of upper shield 63, thus maintaining the seal over all operating temperatures of the sensor 40.

In alternative examples, the gasket 34 may be made of other compliant support materials such as wire mesh, which would be used if the gas-resistant sealing function is not paramount. The gasket 34 may also be a high temperature spring material that may or may not be used in conjunction with a sealing material, depending whether the sealing function is thought necessary in the particular example.

As can be seen, there is no direct non-compliant or non-deformable mounting between the upper shield 63 and the shell 50 or between the lower insulator 48 and the shell 50. Instead, the mounting contact to the shield 63 and its internal components is made vis-à-vis the gasket 34 at the lower end 67 of the upper shield 63 and vis-à-vis the protective shield 90 at the area 94 near the upper end 89 of the upper shield 63. This configuration has been found to reduce the potential for mechanical shock, traveling from the protective shield 90 or the shell 50 to the components internal of the upper shield 63. Of most particular relevance is the glass seal 10, which, when implemented with the structure shown, maintains valid mounting support and sealing functions through severe shock and drop tests demonstrating an overall robustness to the design shown.

Figure 2:
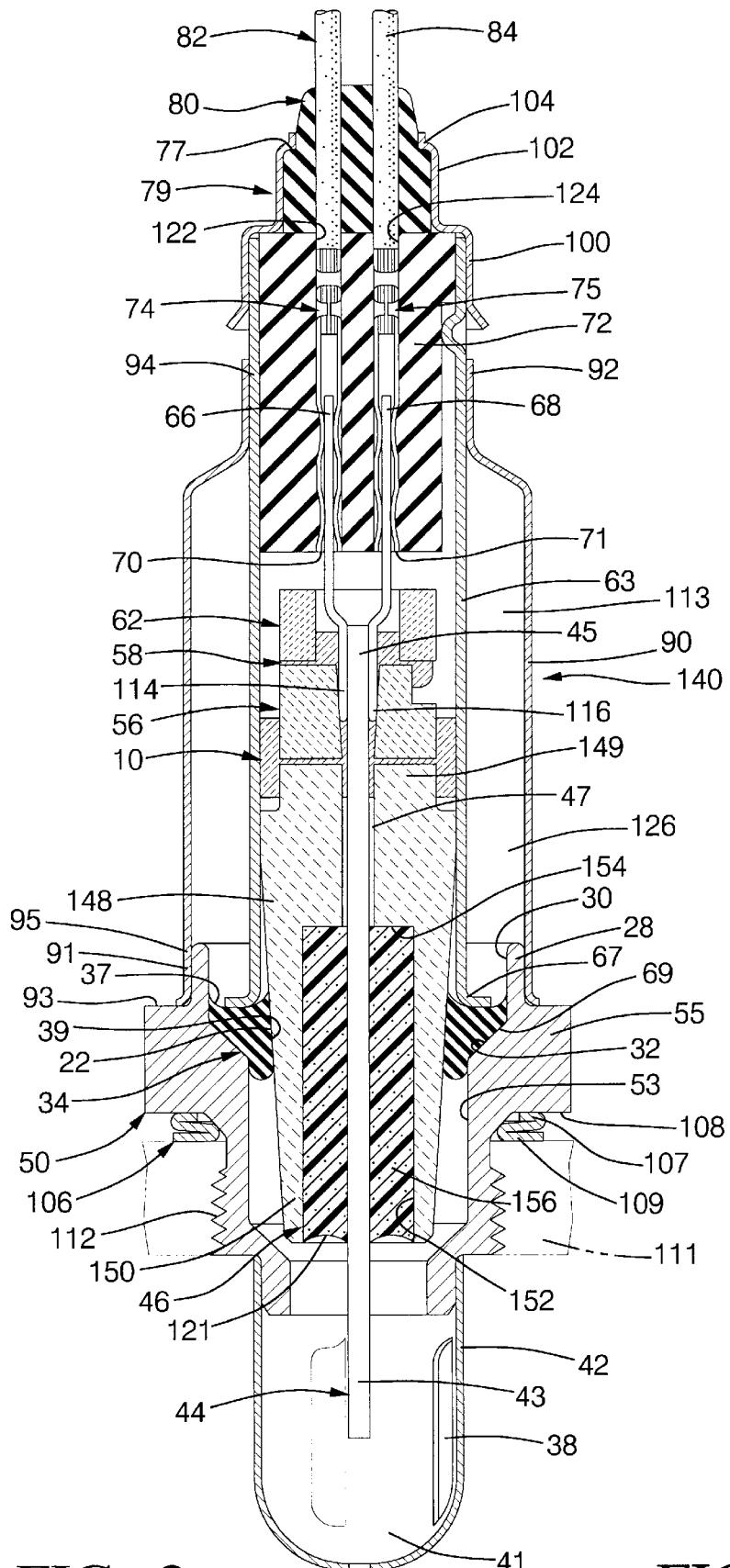
FIG. 2 illustrates a second example oxygen sensor according to this invention.

Referring now to FIG. 2, the example oxygen sensor 140 shown is similar to the oxygen sensor 40 shown in FIG. 1 and like parts are labeled with like reference numerals. The sensor 140 differs from sensor 40 in FIG. 1 in that lower insulator 48 in FIG. 1 is now replaced by lower insulator 148. Lower insulator 148 has the top end 149 engaging the seal 10 and the bottom end 150 positioned adjacent the sensing chamber 41. A cylindrical cavity 152 is formed down the center of lower insulator 148 extending from end 150 of insulator 148 to the radially extending wall 154 defining the upper end of cavity 152. The sensing element 44 extends completely through lower insulator 148, including through cavity 152, so that end 43 extends into the sensing chamber 41.

A compressible supporting material 156 is added so that it annularly surrounds the sensing element 44 within the cavity 152, being packed between the sensing element 44 and the walls of the cavity 152. The support material 156 may be the same type of material used for the gasket 34 or may be any other type of intumescent or other support material durable in a high temperature environment, for example, such as compressible metal mesh. The support material 156 is compliant further improving shock resistance of the sensor, allows for different thermal rates of expansion between the end 43 of the sensing element 44 and the lower insulator 48 and, when the support material 156 has a low heat transfer rate, adds to the thermal isolation between the glass seal and the sensing chamber 41.

Figure 4:
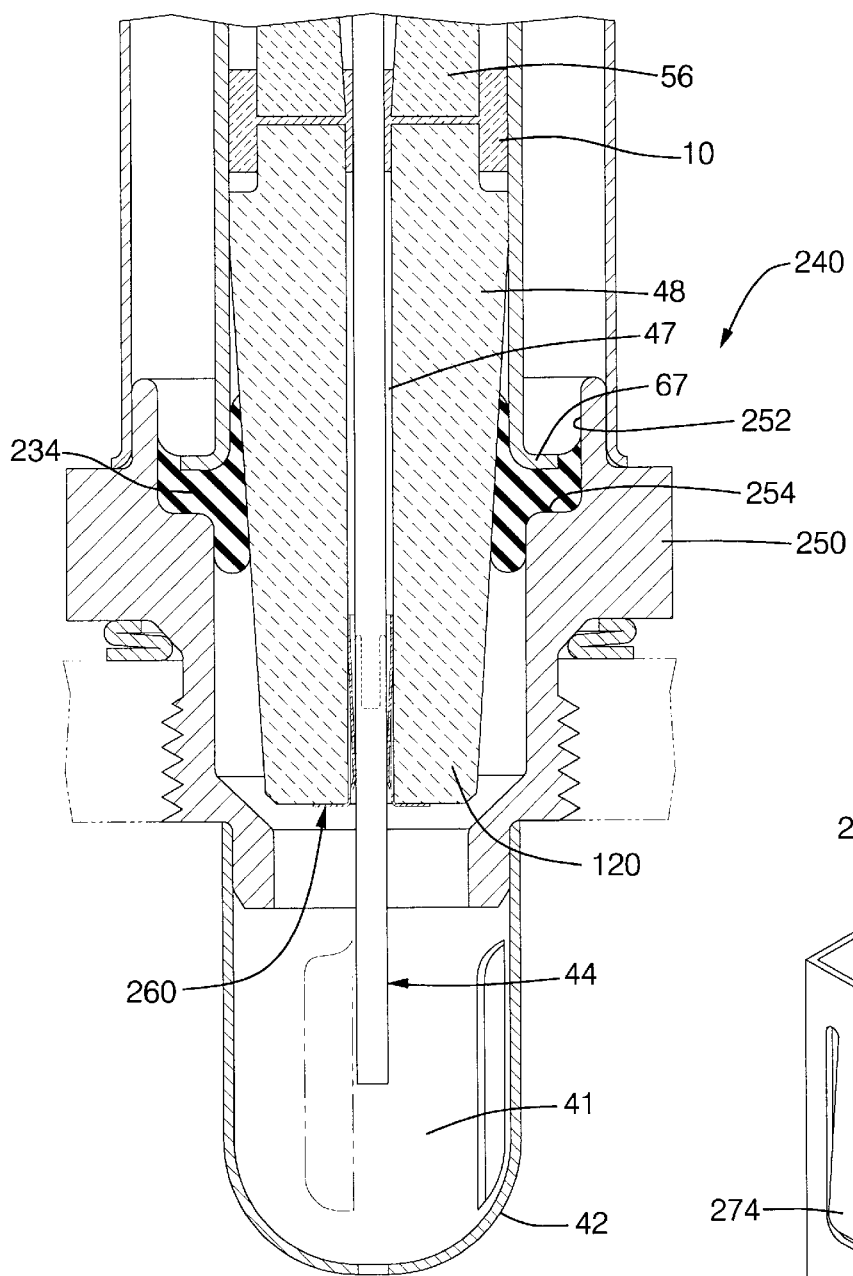
FIG. 4 illustrates a portion of a third example oxygen sensor according to this invention.
Figure 5:
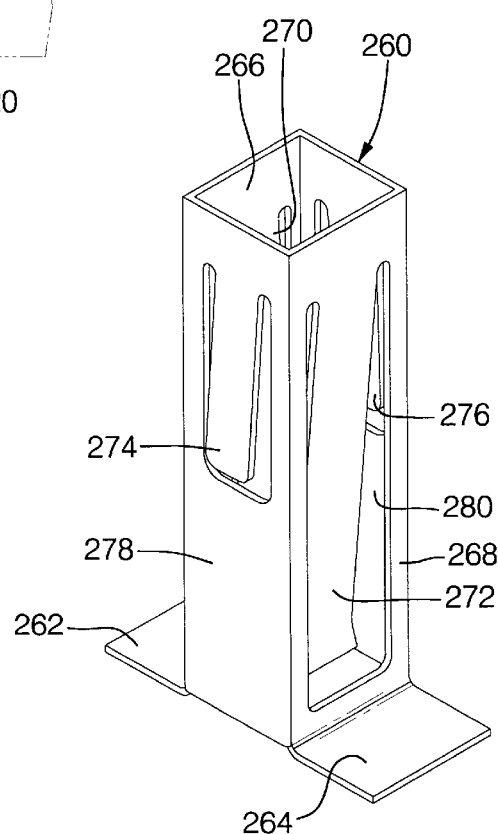
FIG. 5 illustrates a view of spring clip 260 shown in FIG. 4.

Referring now to FIGS. 4 and 5, the sensor 240 shown in FIG. 4 includes a spring clip 260 maintaining a resilient support for the sensor 44 near the sensing chamber 41. The spring clip 260 has sides 266, 268, 278 and 280 that extend into the central opening 47 of the insulator 48. Spring arms 270 and 272 extend in and apply opposing spring forces to opposite planar surfaces of sensor 44 to secure the sensor 44 with some resilience to dampen vibration. Spring arms 274 and 276 extend outward and apply opposing spring forces against the internal walls of opening 47 in insulator 48 to maintain the spring clip 260 in place in insulator 260, with end shoulders 262 and 264 resting against the lower end 120 of the insulator 48.

In the example shown in FIG. 4, the shell 250 does not include the conical surface 32 (FIGS. 1 and 2). Instead, cavity 252 extends with uniform diameter down to shoulder 254 and the gasket 234, similar to gasket 34 in FIG. 3, compresses to the shape of cavity 252 and shoulder 254 as shown.

The spring clip 260 shown is one example and other example spring clips may be used. For example a flat disk may be fixed in place at the lower end 120 of the insulator 48 and bent arms may extend out to apply opposing forces against the sensor 44.

We claim:
1. An oxygen sensor comprising:
    an elongated planar sensing element;
    a tubular shield within which at least a portion of the sensing element extends;
    a seal sealably mounting the sensing element within the tubular shield;
    a shell for mounting the oxygen sensor to a body through which exhaust flows;
    an annular gasket seating (i) at a first surface an end of the tubular shield and (ii) at a second surface an annular seat of the shell, wherein there is no direct contact between the tubular shield and the shell; and
    an outer shield having an upper end affixed to an outer surface of the tubular shield and a lower end affixed to the shell, wherein the outer shield mechanically holds the tubular shield, the annular member and the shell in compressive force engagement.
2. An oxygen sensor according to claim 1 wherein the gasket provides a gas-resistant seal between the tubular shield and the shell.
3. An oxygen sensor according to claim 1, wherein the seal is a glass seal.
4. An oxygen sensor according to claim 1, also comprising a tubular insulator having a central opening through which the sensing element passes and having an exterior surface forming a wedge shape, wherein the exterior surface forming the wedge shape contacts an inner cylindrical surface of the gasket and provides a radially compressive force on the gasket.
5. An oxygen sensor according to claim 1, wherein the annular seat of the shell forms a conical surface that provides a radially compressive force against a radially outer surface of the gasket.
6. An oxygen sensor according to claim 1, wherein the annular gasket comprises a deformable material and wherein the annular gasket expands with heat.
7. An oxygen sensor according to claim 1, wherein the gasket provides a compliant support for the tubular shield within the shell.
8. An oxygen sensor according to claim 1, also comprising
    a tubular insulator having a central opening through which the sensing element extends: and
    a spring clip maintaining resilient support between the sensing element and the tubular insulator.
9. An oxygen sensor according to claim 6, wherein the shell includes an inner conical surface against which the annular gasket is deformed, wherein the inner conical surface orients the gasket in a preferred expansion direction.
10. An oxygen sensor comprising:
    a sensing element with a planar shape;
    a tubular support within which the sensing element is secured;
    a shell through which the oxygen sensor is mounted to a body;
    an annular member providing sealing engagement to the tubular support and to the shell, wherein the tubular support does not directly contact the shell; and
    a tubular outer shield having an upper end affixed to an outer surface of the tubular support and a lower end affixed to the shell, wherein the tubular outer shield mechanically holds the tubular support, the annular member and the shell in compressive force engagement.

11. An oxygen sensor according to claim 10, wherein the annular member is compressed between the tubular support and the shell and wherein the compression deforms the annular member.

12. An oxygen sensor according to claim 10, wherein the tubular support has an end that seats against the annular member.

13. An oxygen sensor according to claim 12, wherein the end extends radially outwardly to form a compressive surface that seats against the annular member.

14. An oxygen sensor according to claim 10, also comprising a glass seal securing the sensing element within the tubular support.

15. An oxygen sensor according to claim 10, also comprising a tubular insulator having a central opening through which the sensing element extends and having an exterior surface forming a wedge shape, wherein the exterior surface forming the wedge shape contacts an inner cylindrical surface of the annular member and provides a radially compressive force on the annular member.

16. An oxygen sensor according to claim 10, wherein the shell includes an inner conical surface that contacts the annular member and provides a radially compressive force against a radially outer surface of the annular member.

17. An oxygen sensor according to claim 10, wherein the annular member comprises a deformable material.

18. An oxygen sensor according to claim 10, wherein the tubular outer shield has a body portion extending radially outwardly from the tubular support.

19. An oxygen sensor according to claim 10, also comprising an insulating support member having a central opening through which the sensing element extends, wherein the insulating support member has a first end proximate to where the sensing element is supported in the tubular support member and a second end proximate to a sensing chamber, wherein a cavity is formed in the second end of the insulating support member, wherein a packing material is located within the cavity to provide additional support to the sensing element.

20. An oxygen sensor according to claim 10, also comprising an insulating support member having a central opening through which the sensing element extends, wherein the insulating support member has a first end proximate to where the sensing element is supported in the tubular support member and a second end proximate to a sensing chamber, wherein the sensing element is supported at the second end by one member of a set comprising: an intumescent support, a ceramic fiber, a wire mesh and a mechanical spring.

* * * * *

UNITED STATES PATENT AND TRADEMARK OFFICE
Certificate

Patent No. 5,817,920            Patented: October 6, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Richard C. Kuisell, Lapeer, MI; David E. Achey, Grand Blanc, MI; Richard W. Duce, Flushing, MI; and Scott M. Ciosek, Grand Blanc, MI.

Signed and Sealed this Sixteenth Day of February, 1999.

HEZRON E. WILLIAMS
*SPE*
Art Unit 2856